(12) United States Patent
Merril et al.

(10) Patent No.: US 6,817,973 B2
(45) Date of Patent: Nov. 16, 2004

(54) APPARATUS FOR CONTROLLING FORCE FOR MANIPULATION OF MEDICAL INSTRUMENTS

(75) Inventors: Gregory L. Merril, Chevy Chase, MD (US); Richard L. Cunningham, Washington, DC (US); J. Michael Brown, Washington, DC (US); Robert F. Cohen, Burtonsville, MD (US); Philip G. Feldman, Catonsville, MD (US)

(73) Assignee: Immersion Medical, Inc., San Jose, CA (US)

(*) Notice: Subject to any disclaimer, the term of this patent is extended or adjusted under 35 U.S.C. 154(b) by 130 days.

(21) Appl. No.: 09/811,358

(22) Filed: Mar. 16, 2001

(65) Prior Publication Data

US 2003/0040737 A1 Feb. 27, 2003

Related U.S. Application Data (60) Provisional application No. 60/189,838, filed on Mar. 16, 2000.

(51) Int. Cl.[7] .............................................. A61B 1/018
(52) U.S. Cl. ...................... 600/118; 600/103; 600/106; 600/117
(58) Field of Search ................................ 600/103, 104, 600/106, 114, 117, 118

(56) References Cited

U.S. PATENT DOCUMENTS

| | | |
|---|---|---|
| 2,972,140 A | 2/1961 | Hirsch |
| 3,157,853 A | 11/1964 | Hirsch |
| 3,220,121 A | 11/1965 | Cutler |
| 3,497,668 A | 2/1970 | Hirsch |
| 3,517,446 A | 6/1970 | Corlyon et al. |
| 3,623,064 A | 11/1971 | Kagan |
| 3,902,687 A | 9/1975 | Hightower |
| 3,903,614 A | 9/1975 | Diamond et al. |
| 3,911,416 A | 10/1975 | Feder |
| 4,127,752 A | 11/1978 | Lowthorp |
| 4,160,508 A | 7/1979 | Salisbury, Jr. |
| 4,236,325 A | 12/1980 | Hall et al. |
| 4,262,549 A | 4/1981 | Schwellenbach |
| 4,333,070 A | 6/1982 | Barnes |
| 4,464,117 A | 8/1984 | Foerst |
| 4,484,191 A | 11/1984 | Vavra |

(List continued on next page.)

FOREIGN PATENT DOCUMENTS

| | | | |
|---|---|---|---|
| EP | 0 349 086 A1 | 1/1990 | |
| EP | 0970714 A2 | 1/2000 | |
| GB | 2252656 A | 8/1992 | |
| GB | 2288686 A | 10/1995 | |
| JP | H2-185278 | 7/1990 | |
| JP | H4-8361 | 1/1992 | |
| JP | H5-192449 | 8/1993 | |
| JP | H7-24147 | 1/1995 | |
| WO | WO 98/03954 A1 | 1/1998 | |
| WO | WO 99/39317 * | 8/1999 | ........... G09B/23/28 |

OTHER PUBLICATIONS

Patrick, "Design, Construction, and Testing of a Fingertip Tactlla Display for Interaction with Virtual and Remote Environments," *Master of Science Thesis*, MIT, Aug. 1990, archived Nov. 8, 1990.

(List continued on next page.)

*Primary Examiner*—John P. Leubecker (57) ABSTRACT

Apparatus and method for controlling force applied to and for manipulation of medical instruments. An elongated member of a medical instrument can be sensed, and an actuator can be used to apply force to the medical instrument for control and manipulation of the instrument. Via use of the applied forces, the instrument can be moved to a desired position in a working channel, haptic indications of position can be output to the user, and/or user control over the instrument can be enhanced.

26 Claims, 4 Drawing Sheets

U.S. PATENT DOCUMENTS

| | | | |
|---|---|---|---|
| 4,513,235 A | 4/1985 | Acklam et al. | |
| 4,581,491 A | 4/1986 | Boothroyd | |
| 4,599,070 A | 7/1986 | Hladky et al. | |
| 4,708,656 A | 11/1987 | de Vries et al. | |
| 4,713,007 A | 12/1987 | Alban | |
| 4,794,392 A | 12/1988 | Selinko | |
| 4,885,565 A | 12/1989 | Embach | |
| 4,891,764 A | 1/1990 | McIntosh | |
| 4,930,770 A | 6/1990 | Baker | |
| 4,934,694 A | 6/1990 | McIntosh | |
| 5,019,761 A | 5/1991 | Kraft | |
| 5,022,384 A | 6/1991 | Freels | |
| 5,022,407 A | 6/1991 | Horch et al. | |
| 5,035,242 A | 7/1991 | Franklin et al. | |
| 5,038,089 A | 8/1991 | Szakaly | |
| 5,078,152 A | 1/1992 | Bond et al. | |
| 5,165,897 A | 11/1992 | Johnson | |
| 5,175,459 A | 12/1992 | Danial et al. | |
| 5,186,695 A | 2/1993 | Mangseth et al. | |
| 5,212,473 A | 5/1993 | Louis | |
| 5,240,417 A | 8/1993 | Smithson et al. | |
| 5,271,290 A | 12/1993 | Fischer | |
| 5,275,174 A | 1/1994 | Cook | |
| 5,283,970 A | 2/1994 | Aigner | |
| 5,299,810 A | 4/1994 | Pierce et al. | |
| 5,309,140 A | 5/1994 | Everett, Jr. et al. | |
| 5,334,027 A | 8/1994 | Wherlock | |
| 5,436,622 A | 7/1995 | Gutman et al. | |
| 5,437,607 A | 8/1995 | Taylor | |
| 5,466,213 A | 11/1995 | Hogan et al. | |
| 5,547,382 A | 8/1996 | Yamasaki et al. | |
| 5,575,761 A | 11/1996 | Hajianpour | |
| 5,623,582 A | 4/1997 | Rosenberg | |
| 5,690,582 A | 11/1997 | Ulrich et al. | |
| 5,766,016 A | 6/1998 | Sinclair et al. | |
| 5,769,640 A | 6/1998 | Jacobus | |
| 5,785,630 A | 7/1998 | Bobick et al. | |
| 5,800,177 A | 9/1998 | Gillio | |
| 5,800,178 A | 9/1998 | Gillio | |
| 5,800,179 A | 9/1998 | Bailey | |
| 6,038,488 A * | 3/2000 | Barnes et al. | 700/161 |
| 6,111,577 A | 8/2000 | Zilles et al. | |
| 6,160,489 A | 12/2000 | Perry et al. | |
| 6,422,941 B1 | 7/2002 | Thorner et al. | |
| 2001/0016804 A1 | 8/2001 | Cunningham et al. | |

OTHER PUBLICATIONS

Calder, "Design of a Force–Feedback Touch–Introducing Actuator For Teleoperator Roborot Control," *Bachelor of Scienco Thesis*, MIT, May 1983, archived Jun. 23, 1983.

Wiker, "Teletouch Display Development: Phase 1 Report," *Technical Report 1230*, Naval Ocean Systems Center, San Diego, Jul. 1988.

Bliss, "Optical–to–Tactile Image Conversion for the Blind," *IEEE Transactions on Man–Machine Systems*, vol. MMS–11. No. 1, Mar. 1970.

Johnson, "Shape–Memory Alloy Tactile Feedback Actuator," *Armstrong Aerospace Medical Research Laboratory*, AAMRL–TR–90–039, Aug. 1990.

Kontarinis et al., "Tactile Display of Vibratory information in Teleopersion and Virtual Environments," PRESENCE, 4(4):387–402, Harvard Univ., 1995.

Aukstakalnis et al., "Silicon Mirage: The Art and Science of Virtual Reality," ISBN 0–938151–82–7, pp. 129–130, 1992.

Eberhardt et al., "Inducing Dynamic Haptic Perception by The Hand: System Description and Some Results," DSC–vol. 55–1, *Dynamic Systems and Control*: vol. 1, ASME 1994.

Gobel et al., "Tactile Feedback Applied to Computer Mice," *International Journal of Human–Computer Interaction*, vol. 7, No. 1, pp. 1–24, 1995.

Pimentel et al., "Virtual Reality: through the new looking glass," $2^{nd}$ Edition, McGraw–Hill, ISBN 0–07–050167–X, pp. 41–202, 1994.

"Cyberman Technical Specification," *Logttech Cyberman SWIFT Supplement to Logttech Mouse Technical Reference and Programming Guide*, Apr. 5, 1994.

Ouhyoung et al., "The Development of a Low–Cost Force Feedback Joystick and its Use in the Virtual Reality Environment," *Proceedings of the Third Pacific Conference on Computer Graphics and Applications, Pacific Graphics '95*, Seoul, Korea, Aug. 21–24, 1995.

Kaczmarek et al., "Tactile Displays," Virtual Environment Technologies, Chap. 9, pp. 349–414.

Lake, "Cyberman from Logitech," at http://www.lblblle,org/GameByles/Issue21/greviews/cyberman.html, 1994.

"Component Maintenance Manual With Illustrated Parts List, Coaxial Control Shaker Part No. C–25502," Safe Flight Instrument Corporation, Revised Jan. 28, 2002 (3 pages).

"Technical Manual Overhaul Instructions With Parts Breakdown, Coaxial Control Shake r Part No. C–25502," Safe Flight Instrument Corporation, Revised Jul. 16, 1980 (23 pages).

Scannell, "Taking a Joystick Ride," *Computer Currents*, Boston Edition, vol. 9, No. 11, Nov. 1994.

Yamakita et al., "Tele–Virtual Realty of Dynamic Mechanical Model," *Proceedings of the 1992 IEEE/RSJ International Conference on Intelligent Robots and Systems*, Raleigh, NC, Jul. 7–10, 1992.

Noll, "Man–Machine Tactile," *SID Journal*, Jul./Aug. 1972 Issue.

Rosenberg, "Virtual Fixtures: Parceptual Overlays Enhance Operator Performance in Telepresence Tasks," *Ph.D. Dissarlation*, Stanford University, Jun. 1994.

Baigrie, "Electric Control Loading—A Low Cost, High Performance Alternative," *Proceedings of Interservice/Industry Traning Systems Conference*, pp. 247–254, Nov. 6–8, 1990.

Iwata, "Pen–based Haptic Virtual Environment," 0–7803–1363–1/93 IEEE, pp. 287–292, 1993.

Russo, "The Design and Implementation of a Three Degree of Freedom Force Output Joystick," *MIT Libraries Archives* pp. 1–131, May 1990, archived Aug. 14, 1990.

Brooks et al., "Hand Controllers for Teleoperation—A State–of–the–Art Technology Survey and Evaluation," *JPL Publication 85–11*, NASA–CR–175890; N85–28559, pp. 1084, Mar. 1, 1985.

Jones et al., "A perceptual analysis of stiffness," ISSN 0014–4819 Springer International (Spinger–Verlag); *Experimental Brain Research*, vol. 79, No. 1, pp. 150–156, 1990.

Burdea et al., "Distributed Virtual Force Feedback, Lecture Notes for Workshop on Force Display in Virtual Environments and its Application to Robotic Teleoperation," *1993 IEEE International Conference on Robotics and Automation*, pp. 25–44, May 2, 1993.

Snow et al., Model–X Force–Reflecting–Hand–Controller, NT Control No. NPO–17851; JPL Case No. 7348, pp. 1–4 with 45 pages of attachments, Jun. 15, 1989.

Ouh–Young, "Force Display in Molecular Docking," Doctoral Dissertation, University of North Carolina at Chapel Hill, UMI Order No. 9034744, p. 1–369, 1990.

Tadros, "Control System Design for a Three Degree of Freedom Virtual Environment Simulator Using Motor/Brake Pair Actuators," *MIT Archive*, pp. 1–88, Feb. 1990, archived Aug. 13, 1990.

Caldwell et al., "Enhanced Tactile Feedback (Tele–Taction) Using a Multi–Functional Sensory System," 1050-4729/93, pp. 955–960, 1993.

Adelstein et al., "Design and Implementation of a Force Reflecting Manipulandum for Manual Control research," DSC–vol. 42, *Advances in Robotics*, pp. 1–12, 1992.

Gotow et al., "Controlled Impedance Test Apparatus for Studying Human Interpretation of Kinesthetic Feedback," WA11–11:00, pp. 332–337.

Stanley et al., "Computer Simulation of Interacting Dynamic Mechanical System Using Distributed Memory Parallel Processors," DSC–vol. 42, *Advances in Robotics*, pp. 55–61, ASME 1992.

Russo, "Controlling Dissipative Magnetic Particle Brakes in Force Reflective Devices," DSC–vol. 42, *Advances in Robotics*, pp. 63–70, ASME 1992.

Kontarinis et al., "Display of High–Frequency Tactile Information to Teleoperators," *Telemanipulator Technology and Space Telerobotics*, Won S. Kim, Editor, Proc. SPIE vol. 2057, pp. 40–50, Sep. 7–9, 1993.

Patrick et al., "Design and Testing of a Non–reactive, Fingertip, Tactile Display for Interaction with Remote Environments," *Cooperative Intelligent Robotics in Space*, Rui J. deFigueiredo et al, Editor, Proc. SPIE vol. 1387, pp. 215–222, 1990.

Adelstein, "A Virtual Environment System for the Study of Human Arm Tremor," *Ph.D. Dissertation*, Dept. of Mechanical Engineering, MIT, Jun. 1989, archived Mar. 13, 1990.

Bejczy, "Sensors, Controls, and Man–Machine Interface for Advanced Teleoperation," *Science*, vol. 208, No. 4450, pp. 1327–1335, 1980.

Bejczy et al., "Generalization of Bilateral Force–Reflecting Control of Manipulators," *Proceedings of Fourth CISM–IFToMM*, Sep. 8–12, 1981.

McAffee et al., "Teleoperator Subsystem/Telerobot Demonstrator: Force Reflecting Hand Controller Equipment Manual," *JPL* 1988, JPL D–5172.

Minsky, "Computational Haptics: The Sandpaper System for Synthesizing Texture for a Force–Feedback Display," *Ph.D. Dissertation*, MIT, Jun. 1995, archived Jul. 6, 1995.

Jacobsen et al., "High Performance, Dextrous Telerobotic Manipulator With Force Reflection," *Intervention/ROV '91 Conference &Exposition*, Hollywood, Florida, May 21–23, 1991.

Shimoga, "Finger Force and Touch Feedback Issue in Dexterous Telemanipulation," *Proceedings of Fourth Annual Conference on Intelligne Robotic Systems for Space Exploration*, Rensselaer Polytechnic Institute, Sep. 30–Oct. 1, 1992.

IBM Technical Disclosure Bulletin, "Mouse Ball–Actuating Device With Force and Tactile Feedback," vol. 32., No. 9B, Feb. 1990.

Terry et al., "Tactile Feedback In A Computer Mouse," *Proceedings of Fourteenth Annual Northeast Bioengineering Conference, University of New Hampshire*, Mar. 10–11, 1988.

Howe, "A Force–Reflecting Teleoperated Hand System for the Study of Tactile Sensing in Precision Manipulation," *Proceedings of the 1992 IEEE International Conference on Robotics and Automation*, Nice, France, May 1992.

Eberhardt et al., "Omar—A Haptic display for speech perception by deaf and deaf–blind individuals," *IEEE Virtual Reality Annual International Symposium*, Seattle, WA, Sep. 18–22, 1993.

Rabinowitz et al., "Multidimensional tactile displays: Identification of vibratory intensity, frequency, and contractor area," *Journal of The Acoustical Society of America*, vol. 82, No. 4, Oct. 1987.

Bejczy et al., "Kinesthetic Coupling Between Operator and Remote Manipulator," *International Computer Technology Conference, The American Society of Mechanical Engineers*, San Francisco, CA, Aug. 12–15, 1980.

Bejczy et al., "A Laboratory Breadboard System For Dual–Arm Teleoperation," *SOAR '89 Workshop, JSC*, Houston, TX, Jul. 25–27, 1989.

Ouhyoung et al., "A Low–Cost Force Feedback Joystick and Its Use in PC Video Games," *IEEE Transactions on Consumer Electronics*, vol. 41, No. 3, Aug. 1995.

Marcus, "Touch Feedback in Surgery," *Proceedings of Virtual Reality and Medicine The Cutting Edge*, Sep. 8–11, 1994.

Bejczy, et al., "Universal Computer Control System (UCCS) For Space Telerobots," CH2413–3/87/0000/0318501.00 1987 IEEE, 1987.

* cited by examiner

APPARATUS FOR CONTROLLING FORCE FOR MANIPULATION OF MEDICAL INSTRUMENTS

CROSS REFERENCE TO RELATED APPLICATIONS

This application claims the benefit of U.S. Provisional Application No. 60/189,838, filed Mar. 16, 2000 by Merril et al., entitled "System and Method for Controlling Force Applied to and Manipulation of Medical Instruments," which is incorporated herein by reference in its entirety.

BACKGROUND OF THE INVENTION

Minimally invasive techniques for providing medical examinations and therapies frequently employ endoscopes, such as a bronchoscope, ureteroscope, or flexible sigmoidoscope. Endoscopes such as these typically employ fiber optic or CCD imaging devices to enable the practitioner to visually inspect otherwise inaccessible areas of the anatomy such as the lungs, the ureter and kidneys, the colon, etc. These endoscopes also typically contain a tube, called the working channel, through which solutions such as anesthetics can be administered and bodily materials such as mucus can be withdrawn, typically via suction. In addition to use in administering and removing liquids or other material, the working channel of an endoscope is used to pass slender instruments to perform other functions at the distal end of the scope, under visual guidance through the endoscope.

Instruments typically used in this manner include forceps for grasping objects or for pinching and removing small tissue samples, biopsy needles for removing deep tissue samples in the lumen of a needle, snares or baskets for capturing and withdrawing objects such as an aspirated peanut from the lungs or a kidney stone from the calyxes of the kidney, and a wide variety of other tools.

Manipulation of these tools requires simultaneous manipulation or stabilization of the endoscope, along with manipulation of the working channel tool itself. The endoscope can typically be maneuvered along three, four or more degrees of freedom, including insertion and withdrawal, rotation, and tip flexion in one or two dimensions (up/down and/or left/right). The working channel tool is maneuvered along an additional two or more degrees of freedom, including insertion/withdrawal, rotation, and tool actuation, etc. Tool actuation can include, for example, opening and closing the jaws of a biopsy forceps, controlling the plunge of a biopsy needle, actuating a cauterization or ablation tool, pulsing a laser, or opening and closing a snare or basket. The tasks of manipulating and stabilizing the three or more degrees of freedom of the endoscope, while simultaneously manipulating the multiple degrees of freedom of the working channel tool are difficult to perform, and frequently the practitioner uses an assistant to manipulate one or more of the degrees of freedom, such as working channel tool actuation.

SUMMARY OF THE INVENTION

The present invention relates to a device or system that extends the functionality of the working channel of an endoscope by adding devices for sensing motion of the working channel tool and for application of motive force to assist the practitioner in manipulation of the instrument in the working channel.

In one mode of use, the system uses drive wheels driven by a motor or other device to permit the practitioner to quickly exchange working channel tools, by smoothly moving the current tool out of the working channel, and then quickly moving in the new tool to a point just short of exiting the working channel. At this point the practitioner takes over and performs the fine motor skills necessary to move the tool out of the endoscope and into a position to interact with the anatomy. In another mode of operation the physician manipulates tools manually and is provided with tactile guidance via a set of driven or braked drive wheels. One form of guidance is the provision of notification that the tool is approaching the end of the endoscope and is about to emerge from the endoscope. A braking or other tactile force would signal nearing the end of the working channel, enabling the user to move the tool quickly within the working channel without danger of moving the tool too rapidly out of the working channel, thereby reducing the risk of damage or injury to tissue adjacent the distal end of the endoscope.

In another embodiment, the sensor and drive assembly is coupled to a catheter through which instruments and tools are passed into the vascular system. For instance, in the process of implantation of a heart pacing lead, the cardiologist must make a number of fine adjustments in the position of a guide catheter, then attempt to stabilize it while inserting an additional element through the lumen of the stabilized catheter. In one mode, the sensor/drive assembly is commanded to maintain a position using passive or active braking force. In another mode, the tip of the catheter is instrumented and an active mechanism commands insertion/retraction and roll increments to stabilize the actual position of the distal end.

In yet another embodiment, the sensor and drive assembly is instrumented with strain gauges or other devices to detect forces encountered at the distal end of the catheter or working channel tool. These forces are then amplified and displayed to the user via a motor or other motive mechanism.

In another embodiment, the sensor and drive assembly detect and modify motions, for example detecting and filtering out high frequency jitter caused by the user. This superstabilization mode is useful in situations where fine motor control is required.

In another embodiment, signals from a device inserted in the working channel are used to command the motive device to maintain a particular quality of electrical contact with the anatomy. In this situation, electrical impedance is changed by the force of contact. A desired quality of contact is initially attained by the physician, then the device is commanded to control contact force automatically to maintain the particular quality of contact.

The above and still further features and advantages of the present invention will become apparent upon consideration of the following detailed description of specific embodiments thereof, particularly when taken in conjunction with the accompanying drawings wherein like reference numerals in the various figures are utilized to designate like components.

DETAILED DESCRIPTION

Figure 1A:
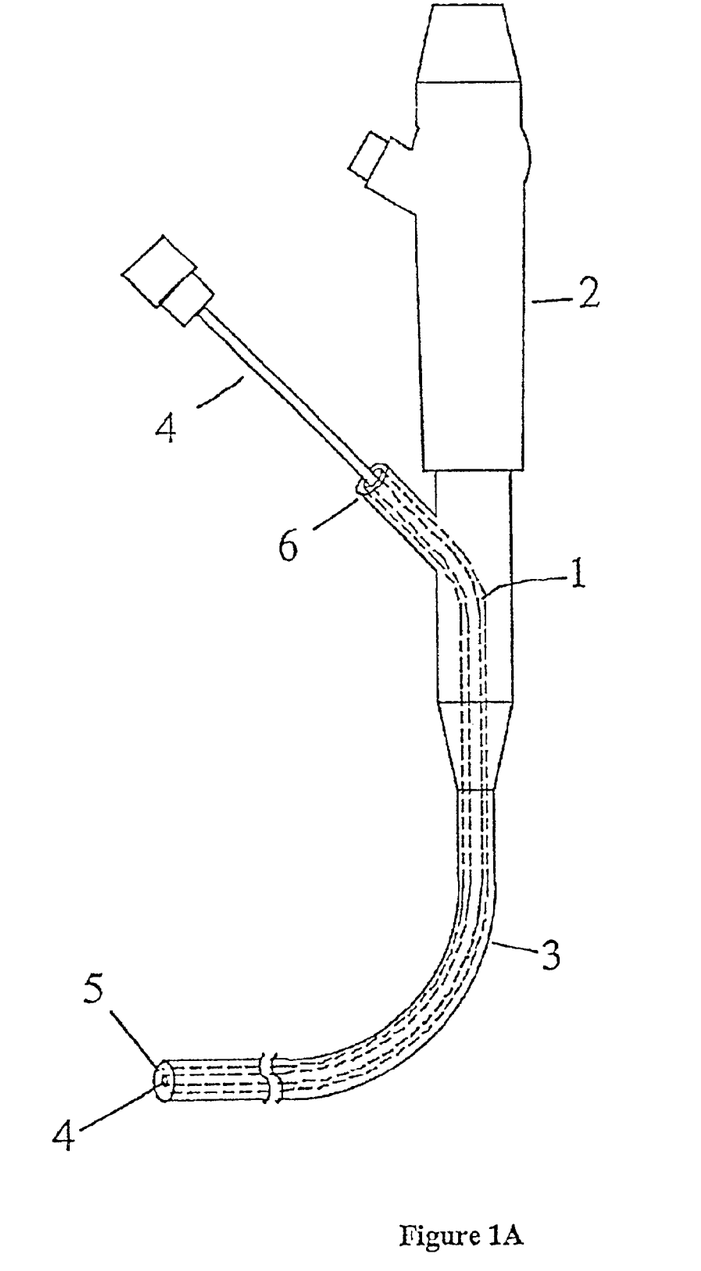
FIG. 1a illustrates an unmodified endoscope with working channel and working channel tool.

FIG. 1a illustrates an unmodified endoscope of the prior art, showing the endoscope body 2 attached to the endoscope tube assembly 3. Working channel tool 4 is inserted into working channel orifice 6 in endoscope body 2. Working channel tool 4 slides through working channel tube 1 and exits the distal end of endoscope tube assembly 3 through working channel orifice 5.

Figure 1B:
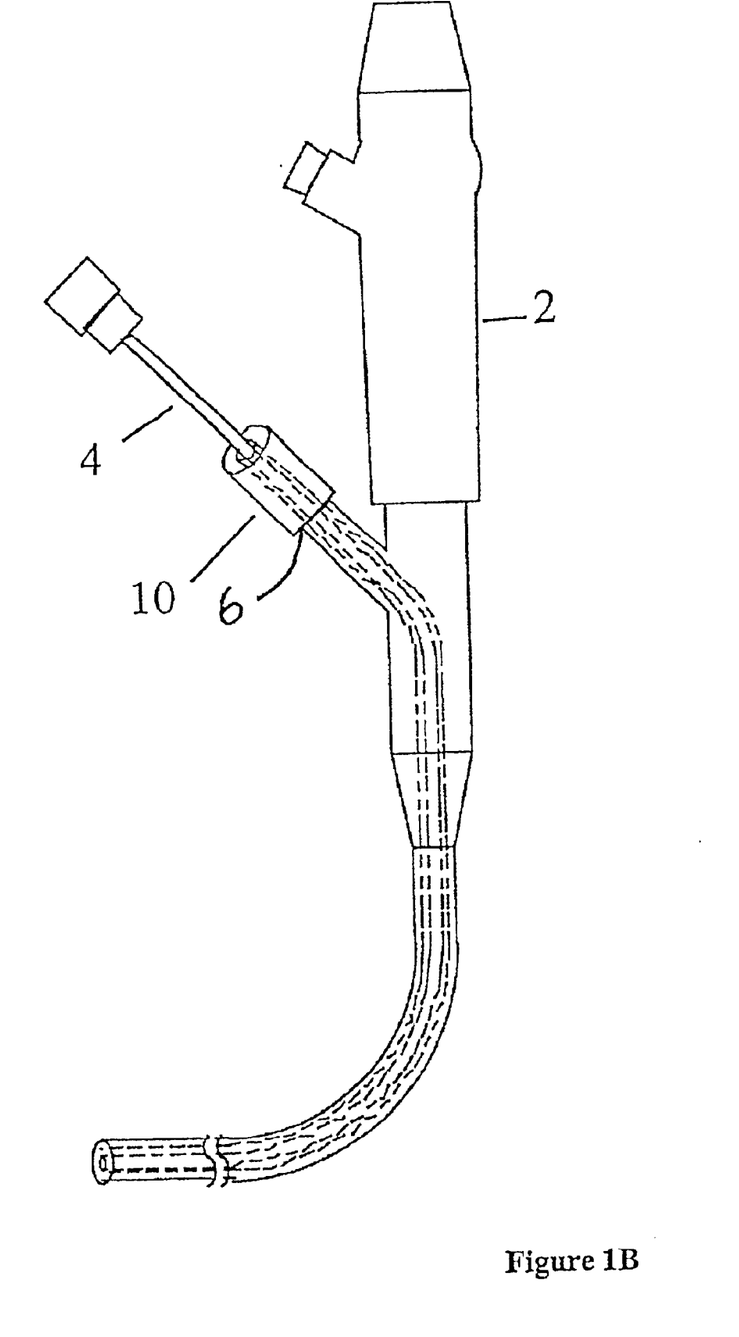
FIG. 1b illustrates an endoscope modified to provide a sensor and control element in accordance with the present invention.

FIG. 1b illustrates one embodiment of a motion sensor and control element 10 of the present invention, which is affixed to the working channel orifice 6 of an endoscope. Working channel tool 4 passes through motion sensor and control element 10 and through working channel orifice 6. Normal manipulation and operation of the working channel to possible through the body of motion sensor and control element 10. Motion sensor and control element 10 can assist in the control of the working channel tool 4, as exemplified in the embodiments presented below.

The working tool 4 may be any of a variety of medical instruments used in endovascular procedures, endoscopy or other medical procedures. For example, the working tool can be a guidewire, a catheter, a heart pacing lead, or a stylet. The tool end that enters and operates on or interacts with the body can include one or more of any of a variety of tools, such as a blade, a serrated edge, a biopsy tool, a trocar tip, an ultrasonic tool, a needle, a vibrating tip, a suturing tool, a retractor, an electrosurgical cutter, an electrosurgical coagulator, a forceps, a needle holder, scissors, an irrigator, an aspirator, a medicator, a laser tool, a cryogenic tool, a flexible steering or guiding tip, and/or a camera. For simplicity, the term "working channel" as used herein is intended to refer to any tube that can guide a medical tool, including catheters, tubes, endoscopic working channels, or other channels.

Figure 2:
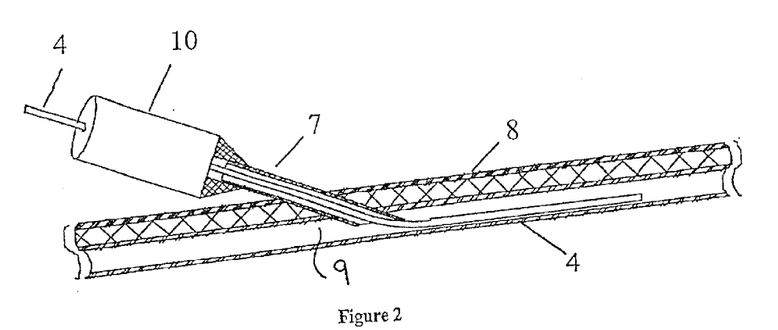
FIG. 2 illustrates an endovascular tool inserted into the vascular anatomy, combined with a sensor and control element in accordance with the present invention.

FIG. 2 illustrates an endovascular application of the motion sensor and control element 10 of the present invention. Motion sensor and control element 10 is coupled to introducer sheath 7 (which can be considered a "working channel" herein), which pierces skin 8 and the wall of blood vessel 9. Elongated endovascular tool 4 passes through motion sensor and control unit 10, through introducer sheath 7, and into the lumen of blood vessel 9.

Figure 3:
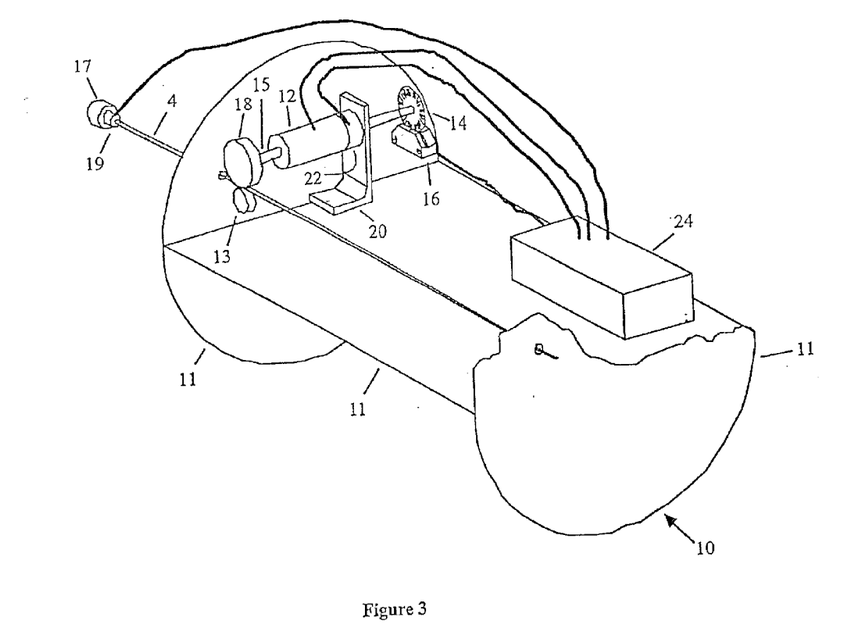
FIG. 3 illustrates an axial motion sensor control element in accordance with the present invention.

FIG. 3 illustrates one embodiment of sensor and control element 10 which measures the motion of and applies force to the body of the working channel tool 4 in its translational degree of freedom. Motion sensor and control element 10 contains a sensor device for measuring translational motion of the body of working channel tool 4. As the elongate portion of working channel tool 4 passes between motion sensing and control wheel 18 and idler wheel 13, it causes rotation of each wheel. Wheel 18 is affixed to shaft 15 of an actuator 12 that is supported by bracket 20. In turn, transparent optical encoder disk 14 is affixed to the opposite end of motor shaft 15. Encoder reader 16 passes light through transparent encoder disk 14. As transparent encoder disk 14 rotates, marks imprinted on the surface pass in front of the light source, occluding alternately light passing through the disk. A plurality of light sensors in encoder reader 16 measure the varying light and dark patterns and determine the amount and direction of rotational motion of encoder disk 14. Control unit 24 receives motion signals from encoder reader 16 corresponding to translational motion of working channel tool 4.

Actuator 12 is operative to provide forces on the working channel tool 4 in its translational degree of freedom, as transmitted by control wheel 18 to the tool 4. The actuator 12 is controlled by control signals from the control unit 24. In some embodiments, the control unit 24 can determine the amount of force to be output from actuator 12 by examining the current signals from the encoder reader 16 indicating the current position or motion of the tool 4, and then control the actuator 12 to output that force. For example, the current position of the tool 4 may indicate when force is to be output and/or the amount of force to be output, as described below.

Control unit 24 can include a microprocessor, ASIC, or other type of processor or controller, for example. Other types of sensors, besides the optical type of sensor described above, can also be used to sense the position and/or amount of motion of working channel tool 4 to determine insertion distance; for example, analog potentiometers, other types of optical sensors, magnetic sensors, etc., can be used. Some embodiments may use absolute sensors instead of the relative sensor described above; for example, successive markings can be placed on the tool 4 and detected by an optical or other type of detector when the markings are moved past the sensor to determine the position of the tool. Actuator 12 is an electronically-controlled device that modifies the force on the tool 4. For example, actuator 12 can be a DC motor, stepper motor, moving magnet actuator, voice coil, hydraulic or pneumatic actuator, or a variety of other types of actuators able to output a force on the working tool 4. Actuator 12 can also be a passive actuator, such as a magnetic particle brake, fluid brake, or other form of brake, which causes a controllable resistance to motion of the tool 4 based on control signals from control unit 24. Multiple actuators 12 may also be used, of same or differing types.

In one mode of the present invention, the total distance of insertion of the working channel tool is measured and controlled by the motion sensor and control element. For example, control unit 24 can be provided with, or can measure (using the sensor) the total insertion distance of working channel tool 4. This distance can be used in assisting control of the tool 4. For example, the user or practitioner can manually move the tool 4 within the working channel. However, when a preset limit, point, or distance is approached by the front (distal) end of the tool, such as the exit point of the channel, control signals can be transmitted to actuator 12 to produce torque necessary to slow and then halt further motion of motion sensing and control wheel 18, thereby slowing and then halting further insertion of working channel tool 4.

In other modes of operation, if the practitioner inserts a tool into the working channel, the actuator 12 can be used to move the tool 4 into and through the working channel, to a point just short of exiting the channel, so that the tool is then ready for manual use by the practitioner, i.e. the practitioner then moves the tool out of the endoscope and into a position to interact with the anatomy. The control unit 24 can use the signals from sensor of the element 10 to determine the position of the tool. In some embodiments, the drive wheel driven by actuator 12 can permit the practitioner to quickly exchange working channel tools, by smoothly moving a current tool out of the working channel, and then quickly moving in the newly-inserted tool to a point just short of exiting the working channel at its other end.

In yet another mode of operation, the physician can manipulate the tools manually and is provided with tactile guidance via the actuator 12. One form of guidance is the provision of a haptic notification that the tool is approaching or has approached a desired location or has traveled a predetermined distance. For example, the haptic notification can indicate that the tool has reached the end of the working channel or catheter and is about to emerge from the channel. A braking or resistive force, or other tactile force, can signal that the tool is nearing the end of the working channel, enabling the user to move the tool quickly within the working channel without danger of moving the tool too rapidly out of the working channel, thereby reducing the risk of damage or injury to tissue adjacent the distal end of the endoscope. The notification can take a variety of forms, from a single pulse of resistance, a barrier force (continuing resistive force), a vibration, damping force (having a magnitude based on velocity of the tool in one or more directions), spring force, a series of particular jolts or actuated detents, etc. In another embodiment, the notification can indicate each increment or predetermined distance that the tool has been moved by the user. For example, a detent, vibration, or jolt can be output by actuator 12 for each 10 centimeters that the tool is moved into the working channel, or the notification can occur at half or quarter points along the channel.

In another embodiment, the sensor and control element 10 can provide forces on a catheter through which instruments and tools are passed into the vascular system. For instance, in the process of implantation of a heart pacing lead, the cardiologist must make a number of fine adjustments in the position of a guide catheter, then attempt to stabilize it while inserting an additional element (such as a lead tool) through the lumen of the stabilized catheter. In one mode, the sensor and control element 10 can be commanded to output forces on the catheter to maintain it at a desired position using passive or active force from actuator 12. In another embodiment, the tip of the catheter can be instrumented and an active mechanism may command insertion/retraction and roll increments of the catheter to stabilize the actual position of the distal end.

In another embodiment, the sensor and control element 10 can detect and modify motions of the working tool 4. For example, the sensor of element 10 can detect high frequency jitter caused by the user, based on short, undesired motions or oscillations the user may be conveying to the tool. These motions can then be filtered out after being detected by providing a force in the opposite direction by actuator 12 to cancel or reduce the magnitude of the jitter. This superstabilization mode can be useful in situations where fine motor control is required.

In another embodiment, signals from a device or tool inserted in the working channel are used to command the motive device/tool to maintain a particular quality of electrical contact with the anatomy, e.g. in a heart pacing lead application. For this type of situation, electrical impedance is typically changed if the magnitude of the force of contact of the tool with the anatomical part is changed. The present invention can be used to maintain or achieve a desired quality of contact (or contact force). For example, a desired quality of contact can be initially attained by the physician using the tool manually. Then, the sensor and control element 10 can be commanded to control the contact force automatically to maintain that particular quality of contact by detecting the electrical impedance resulting from the desired contact; if the electrical impedance goes above or below a desired threshold, the force on the tool from actuator 12 is adjusted to provide the desired electrical contact. Other embodiments may use a force sensor on the distal end of the tool to detect the current contact force and maintain a desired contact force.

In another embodiment of the invention, the forces on the working channel tool 4 applied by the user are measured and used in force determination, where motion sensing and control unit 10 can effectively amplify or reduce forces applied by the user to tool 4. In this embodiment, handle 17 can be disposed adjacent force-torque sensor 19 which in turn is disposed adjacent working channel tool 4 such that translational force applied by the user to working channel tool 4 via handle 17 is sensed by force-torque sensor 19. A control algorithm described below and residing in control unit 24 receives signals resulting from applied force measured by force-torque sensor 19 and in response produces control signals which are transmitted to actuator 12 to control the motion of wheel 18. Wheel 18 can be moved either by force applied by actuator 12 or by frictional forces applied via working channel tool 4. When working channel tool 4 is held motionless by the user, force applied to wheel 18 via shaft 15 of actuator 12 is opposed by, and therefore sensed by, torque sensor 22 which is attached to bracket 20 which is in turn fastened to base 11 of sensing and control element 10. Force applied to working channel tool 4 by control wheel 18 is sensed by torque sensor 22 and denoted $F_W$. This force is added to force applied by the user ($F_U$) to produce the effective force at the distal end of the working channel tool $F_{WC}$, as expressed in the following equation of equilibrium:

$$F_{WC} = F_U + F_W \qquad \text{Equation 1}$$

The control algorithm described below and contained in controller 24 dynamically modifies the force applied by the wheel 18, $F_W$, to control working channel tool force, $F_{WC}$ in response to force applied by the user $F_U$. In particular, if the desired relationship between user applied forces and working tool forces is expressed by function f( ) as:

$$F_{WC} = f(F_U) \qquad \text{Equation 2}$$

Combining these equations and solving for Fw provides the following control algorithm:

$$Fw = f(Fu) - F_U \qquad \text{Equation 3}$$

Control unit 24 receives signals corresponding to user applied force $F_U$ and control wheel force $F_W$ and adjusts control signals transmitted to actuator 12 to implement the control algorithm of equation 3.

In a different embodiment, the sensor and control element 10 can be instrumented with strain gauges or other devices to detect or measure forces encountered at the distal end of the catheter or working channel tool. These forces can then be amplified and displayed to the user via actuator 12 or other motive mechanism to allow the practitioner to more easily control or determine the behavior of the distal end of the moved catheter or tool.

Figure 4:
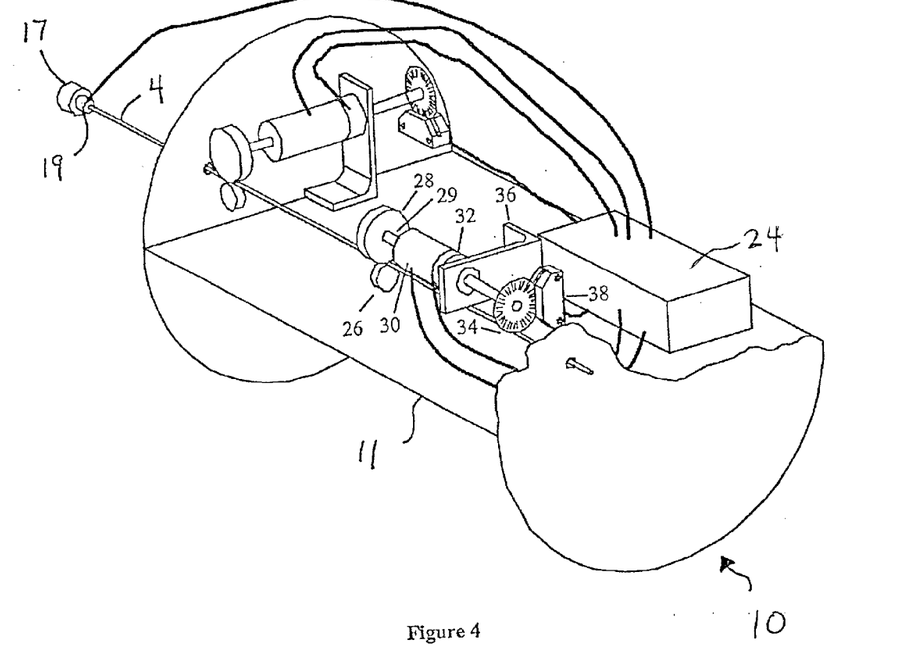
FIG. 4 illustrates addition of a rotational motion sensor and control element to the device in FIG. 3.

FIG. 4 illustrates another embodiment of the sensing and control element 10 of the present invention, in which rotation and torque of the tool 4 is sensed and controlled in addition to sensing translation and controlling axial force as described in FIG. 3. In FIG. 4, as the elongated portion of working channel tool 4 rotates between motion sensing and control wheel 28 and idler wheel 26, it causes rotation of each wheel. Wheel 28 is affixed to shaft 29 of actuator 30. In turn, transparent optical encoder disk 34 is affixed to the opposite end of motor shaft 29 of actuator 30. In turn, transparent optical encoder disk 34 is affixed to the opposite end of motor shaft 29. Encoder reader 38 passes light through transparent encoder disk 34. As transparent encoder disk rotates, marks imprinted on the surface pass in front of the light source, occluding alternately light passing through the disk. A plurality of light sensors in encoder reader 38 measure the varying light and dark patterns and determine the amount and direction of rotational motion of encoder disk 34. Control unit 24 receives motion signals from encoder reader 38 corresponding to rotational motion of working channel tool 4. Control unit 24 measures the rotation of working channel tool 4 using these signals.

Actuator 30 can be similar to actuator 12, where control unit 24 provides control signals to actuator 30 to output a force in the rotational degree of freedom of the tool 4. As described above, both the sensor 34/38 and actuator 30 can take a variety of different forms.

In one embodiment, when a preset limit to rotation is approached by the tool 4, a control signal is produced by control unit 24 and transmitted to actuator 30 to produce torque necessary to slow and then halt further motion of motion sensing and control wheel 28, thereby slowing and then halting further rotation of working channel tool 4. Other embodiments can be similar to those described above for the translational sensing and actuation of the tool 4; for example, a haptic indication can be output to the user when the tool 4 is rotated a predetermined rotational distance (e.g., number of degrees).

In some embodiments of element 10 of FIG. 4, the torque applied by the user to working channel tool 4 can be measured, and motion sensing and control unit 10 can be used to amplify or reduce the torques applied by the user to tool 4. In FIG. 4, the handle 17 is disposed adjacent a force-torque sensor 19 which in turn is disposed adjacent working channel tool 4 such that rotational force applied by the user to working channel tool 4 via handle 17 is sensed by force-torque sensor 19. A control algorithm described below and residing in control unit 24 receives signals resulting from applied force measured by force-torque sensor 19 and in response produces control signals which are transmitted to actuator 30 to control the motion of wheel 28. Wheel 28 can be moved either by force applied by motor 12 or by frictional forces applied via working channel tool 4. When working channel tool 4 is held motionless by the user, force applied to wheel 28 via shaft 29 of actuator 30 is opposed by, and therefore sensed by torque sensor 32 which is attached to bracket 36 which is in turn fastened to base 11 of sensing and control element 10. Torque applied to working channel tool 4 by control wheel 28 is sensed by torque sensor 32 and denoted $T_W$. This torque is added to torque applied by the user ($T_U$) to produce the effective torque at the distal end of the working channel tool $T_{WC}$, as expressed in the following equation of equilibrium:

$$T_{WC}=T_U+T_W \quad \text{Equation 4}$$

The control algorithm described below and contained in controller 24 dynamically modifies the torque applied by the wheel 28, $T_W$, to control working channel tool torque, $T_{WC}$, in response to force applied by the user $T_U$. In particular, if the desired relationship between user applied torque and working tool torque is expressed by function q( ) as:

$$T_{WC}=q(T_U) \quad \text{Equation 5}$$

Combining these equations and solving for Tw provides the following control algorithm:

$$T_W=q(T_U)-T_U \quad \text{Equation 6}$$

Control unit 24 receives signals corresponding to user applied torque $T_U$ and control wheel torque $T_W$ and adjusts control signals transmitted to motor 30 to implement the control algorithm of equation 6.

The sensor 19 can include two sensors in appropriate embodiments: one sensor to measure the axial force applied by the user to the tool 4, and another sensor to measure the torque applied to the user to the tool 4.

Thus, sensing and control unit 10 as shown in FIG. 4 can provide rotational or translational position control, as well as translational force and rotational torque control to working channel tools. As shown in FIG. 2, sensing and control unit 10 can be used to control any elongated medical instrument, such as a catheter used in interventional radiology.

While this invention has been described in terms of several preferred embodiments, it is contemplated that alterations, permutations, and equivalents thereof will become apparent to those skilled in the art upon a reading of the specification and study of the drawings. For example, many different types of sensors and actuators can be used to sense tool position or motion and to output tactile sensations to the user. Furthermore, many of the features described in one embodiment can be used interchangeably with other embodiments. Furthermore, certain terminology has been used for the purposes of descriptive clarity, and not to limit the present invention.

What is claimed is:

1. An apparatus, comprising:

an elongated member having a distal portion configured to engage tissue in a body and having a manipulable proximal portion, said elongated member configured to be moved in a degree of freedom;

a sensor configured to detect a position of the elongated member and output a position signal based on the position;

a controller coupled to the sensor, the controller configured to output a force signal based on the position signal; and an actuator configured to apply a haptic feedback to the elongated member based on the force signal, the haptic feedback operative to indicate when the distal portion of the elonaated member has been translated to an end of a working channel that guides the elongated member.

2. The apparatus of claim 1, wherein the degree of freedom is a translational degree of freedom.

3. The apparatus of claim 1, wherein the degree of freedom is a rotational degree of freedom.

4. The apparatus of claim 1, wherein the haptic feedback includes at least one of a detent force, a vibration, a barrier force, a damping force, and a spring force.

5. The apparatus of claim 1, wherein the elongated member includes at least one of a guidewire, a catheter, a heart pacing lead, and a stylet.

6. The apparatus of claim 1, wherein the distal portion of the elongated member includes at least one of a blade, a serrated edge, a biopsy tool, a trocar tip, an ultrasonic tool, a needle, a vibrating tip, a suturing tool, a retractor, an electrosurgical cutter, an electrosurgical coagulator, a forceps, a needle holder, scissors, an irrigator, an aspirator, a medicator, a laser tool, a cryogenic tool, a flexible steering or guiding tip, and a camera.

7. The apparatus of claim 1, wherein said sensor is further configured to detect a movement of the elongated member in the degree of freedom and output a movement signal based on the movement, the force being applied as a haptic feedback based on the movement signal.

8. The apparatus of claim 1, wherein the haptic feedback is applied to the elongated member before the elongated member exits a distal end of the working channel.

9. An apparatus, comprising;
an elongated member having a distal portion configured to engage tissue in a body and a manipulable proximal portion, said proximal portion configured to be moved in a degree of freedom;
a sensor configured to detect a first force applied to the elongated member in the degree of freedom and to output a sensor signal based on the first force;
a controller in communication with the sensor and the actuator, the controller configured to output a force signal based on the sensor signal; and
an actuator configured to apply a second force to the elongated member in the degree of freedom based on the force signal, the second force being operative to indicate when the distal portion of the elongated member has been translated to an end of a working channel that guides the elongated member.

10. The apparatus of claim 9, wherein the degree of freedom is translational.

11. The apparatus of claim 9, wherein the degree of freedom is rotational.

12. The apparatus of claim 11, wherein the second force is a rotational force.

13. The apparatus of claim 9, wherein the controller is programmable.

14. The apparatus of claim 9, wherein a magnitude of the second force is from about 10 percent to about 90 percent of the first force detected by the sensor.

15. The apparatus of claim 14, wherein the second force is applied in a direction opposite an insertion direction of the elongated member.

16. The apparatus of claim 9, further comprising an outer member having an orifice into which the elongated member is insertable, the actuator being disposed within the orifice.

17. The apparatus of claim 16, wherein the outer member is an endoscope and the orifice is a working channel of the endoscope.

18. The apparatus of claim 16, wherein the outer member is an introducer sheath and the elongated member is an endovascular instrument.

19. The apparatus of claim 18, wherein the endovascular instrument includes at least one of a guidewire, a catheter, a heart pacing lead, and a stylet.

20. The apparatus of claim 9, wherein the actuator is configured to apply the second force to be additive to the first force applied to the elongated member.

21. The apparatus of claim 9, wherein the actuator is configured to apply the second force to counteract the first force applied to the elongated member by the user.

22. The apparatus of claim 9, the sensor being a first sensor, the apparatus further comprising a second sensor coupled to the actuator, the second sensor configured to detect the second force.

23. The apparatus of claim 9, further comprising a position detector coupled to the elongated member, the position detector configured to detect a relative insertion position of the elongated member.

24. The apparatus of claim 9, wherein the distal portion comprises at least one of a blade, a serrated edge, a biopsy tool, a trocar tip, an ultrasonic tool, a needle, a vibrating tip, a suturing tool, a retractor, an electrosurgical cutter, an electrosurgical coagulator, a forceps, a needle holder, scissors, an irrigator, an aspirator, a medicator, a laser tool, a cryogenic tool, a flexible steering or guiding tip, and a camera.

25. The apparatus of claim 9, the sensor being a first sensor, the actuator being a first actuator, the apparatus further comprising:
a second sensor configured to detect a rotational force being applied to the elongated member; and
a second actuator configured to apply a rotational force to the elongated member.

26. An apparatus, comprising:
an elongated member having a distal portion configured to engage tissue in a body and a manipulable proximal portion, said proximal portion configured to be moved in a degree of freedom;
a sensor configured to detect a first force applied to the elongated member in the degree of freedom and to output a sensor signal based on the first force;
a controller in communication with the sensor and the actuator, the controller configured to output a force signal based on the sensor signal; and
an actuator configured to apply a second force to the elongated member in the degree of freedom based on the force signal, the second force being operative to indicate when the distal portion of the elongated member has been translated to an end of a working channel that guides the elongated member, the second force being additive to the first force applied to the elongated member.

* * * * *